US012765768B2

(12) United States Patent
Sinha et al.

(10) Patent No.: US 12,765,768 B2
(45) Date of Patent: Oct. 20, 2026

(54) VISUAL ACUITY MEASUREMENT IN VIRTUAL REALITY HEADSET

(71) Applicant: Verily Life Sciences LLC, Dallas, TX (US)

(72) Inventors: Supriyo Sinha, Menlo Park, CA (US); Dimitri Azar, Chicago, IL (US)

(73) Assignee: Verily Life Sciences LLC, Dallas, TX (US)

( * ) Notice: Subject to any disclaimer, the term of this patent is extended or adjusted under 35 U.S.C. 154(b) by 242 days.

(21) Appl. No.: 18/625,091

(22) Filed: Apr. 2, 2024

(65) Prior Publication Data

US 2025/0302299 A1 Oct. 2, 2025

(51) Int. Cl.

| | |
|---|---|
| ***A61B 3/103*** | (2006.01) |
| ***A61B 3/00*** | (2006.01) |
| ***A61B 3/113*** | (2006.01) |
| ***A61B 3/14*** | (2006.01) |
| ***A61B 90/50*** | (2016.01) |
| ***G06F 3/01*** | (2006.01) |

(52) U.S. Cl.
CPC .............. *A61B 3/103* (2013.01); *A61B 3/005* (2013.01); *A61B 3/113* (2013.01); *A61B 3/14* (2013.01); *A61B 2090/502* (2016.02); *G06F 3/013* (2013.01)

(58) Field of Classification Search
CPC ......... A61B 3/103; A61B 3/005; A61B 3/113; A61B 3/14; A61B 2090/502
USPC .......................................................... 351/223
See application file for complete search history.

(56) References Cited

U.S. PATENT DOCUMENTS

| | | | | |
|---|---|---|---|---|
| 5,583,795 | A * | 12/1996 | Smyth | A61B 3/0025 702/92 |
| 10,231,614 | B2 | 3/2019 | Krueger | |
| 10,545,341 | B2 | 1/2020 | Samec et al. | |
| 10,877,556 | B2 | 12/2020 | Berkner-Cieslicki et al. | |
| 11,612,316 | B2 | 3/2023 | Zidan et al. | |
| 11,696,073 | B2 | 7/2023 | Spector | |
| 2020/0397288 | A1 * | 12/2020 | Zidan | G02B 27/0093 |
| 2021/0030270 | A1 * | 2/2021 | Goyal | G06V 40/18 |
| 2021/0089118 | A1 | 3/2021 | Jaeken et al. | |
| 2021/0330185 | A1 | 10/2021 | Krukowski et al. | |
| 2023/0061866 | A1 * | 3/2023 | Ouderkirk | G02B 27/0172 |

(Continued)

FOREIGN PATENT DOCUMENTS

| | | | |
|---|---|---|---|
| KR | 10-1966164 B1 | 4/2019 | |
| WO | WO-2016149416 A1 * | 9/2016 | A61B 3/005 |

OTHER PUBLICATIONS

International Search Report and Written Opinion received for PCT Patent Application No. PCT/US2023/016983, mailed on Jun. 22, 2023, 10 pages.

*Primary Examiner* — Sharrief I Broome
(74) *Attorney, Agent, or Firm* — Christensen O'Connor Johnson Kindness PLLC

(57) ABSTRACT

An eye examination apparatus comprising: a virtual reality device configured to be worn on a user's head, the virtual reality device having a housing containing a lens and a display operable to display an image to an eye of the user; and a long-pass filter arranged between the lens and the eye for examining the eye's ability to see the image, the long-pass filter having a first transmission region that transmits a visible light and a near-infrared light to the eye and a second transmission region that transmits the near-infrared light and blocks the visible light.

18 Claims, 3 Drawing Sheets

(56) References Cited

U.S. PATENT DOCUMENTS

| | | | |
|---|---|---|---|
| 2023/0200644 | A1 | 6/2023 | Mansouri et al. |
| 2023/0309816 | A1 | 10/2023 | Sinha et al. |

* cited by examiner

FIG. 4
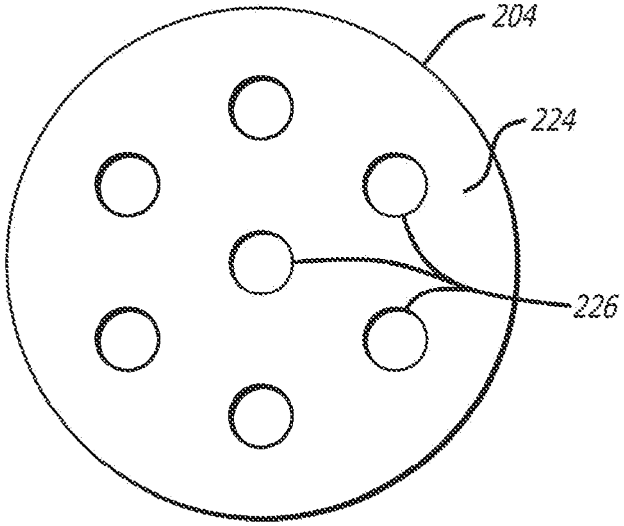
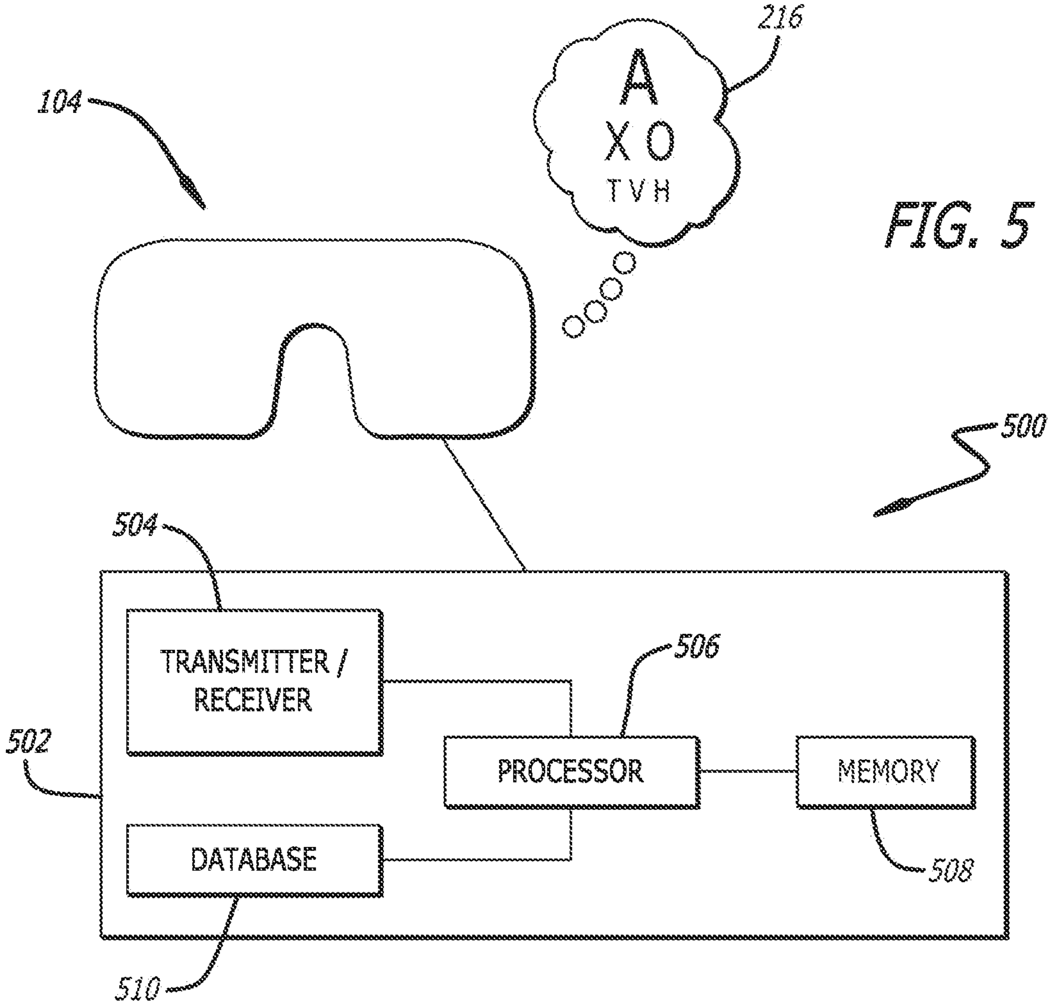
FIG. 5

VISUAL ACUITY MEASUREMENT IN VIRTUAL REALITY HEADSET

FIELD

The subject matter of this disclosure relates to techniques for measuring visual acuity of a human user, using a virtual reality, VR, headset worn by the user.

BACKGROUND

Visual acuity is one of the most common measurements done at the office of an eye care professional (ECP). Eye examinations have been suggested to be performed with a head-worn VR unit. The user puts on the VR head unit, and the ECP operates software that configures the display inside the VR head unit to display various visual elements whose shape, color or size is selected for the test. The user provides feedback to the ECP on how they perceive the visual elements.

SUMMARY

An aspect of the disclosure relates to measuring visual acuity (e.g., to at least the 20/20 level) with an otherwise relatively standard consumer-grade VR headset that has been modified as described below. Representatively, the pinhole test is an important visual acuity test as it can separate vision that can be corrected with lenses versus vision that cannot be corrected because the degradation is due to higher order aberrations or scattered light. The pinhole test is usually done with an ECP to determine if more involved visual acuity measurements need to be made. The test typically involves the ECP placing a pinhole occluder, which is an opaque disk with a small pinhole through it, over one eye of the patient while the other eye is completely covered. The pinhole occluder focuses light through the center of the eye's lens while temporarily removing the effects of refractive errors such as myopia. Since the light passes only through the center of the eye's lens, defects in the shape of the lens (e.g., errors of refraction) have no effect. The patient is then asked to use the eye covered with the pinhole occluder to identify letters, symbols, etc. that get progressively smaller until the patient can no longer identify them. The ECP can then use this information to determine the visual acuity of the patient's eye (e.g., based on the sharpness or clearness of the eyesight when identifying the letters, symbols, etc.) and estimate the maximum improvement in a patient's vision that can be attained by lenses to correct errors of refraction (if any).

The instant disclosure therefore proposes incorporating a custom filter into the VR headset that allows the headset to be used to perform the pinhole test and measure pinhole visual acuity. In some aspects, the custom filter may be permanently or removably positioned between the eyes and the headset. The custom filter may be positioned as close to the eyes as possible. In some aspects, the custom filter may be a long-pass filter that allows for the passage of certain light wavelengths while blocking others. Representatively, the long-pass filter may be formed by a glass disk or substrate and have a single pinhole or an array of pinholes that are cut through the glass disk. In some aspects, an array of pinholes may be formed through the long-pass filter to allow for more light to enter the eye as well as improved field of view compared to a single pinhole. The array of pinholes may allow for the transmission of both visible light and near-infrared light through the filter. The remainder of the filter may allow for the transmission of near-infrared light while blocking the transmission of visible light. In this aspect, eye tracking which typically occurs in VR headsets using near-infrared light can still be performed. For example, the VR headset may track the motion of the user's eyes so that the user can select choices by "clicking" a button with their eyes. In other aspects, instead of cutting holes through the glass, the glass could be etched so that a transmission of near-infrared light through all portions of the filter is approximately equal. The user may then look through the custom pinhole filter at an image displayed by the VR headset and the visual acuity of the eyes may be measured. In some aspects, the pinhole test may be performed in combination with other visual tests being performed by the VR headset.

Representatively, in some aspects, the disclosure is directed to an eye examination apparatus including a virtual reality device configured to be worn on a user's head, the virtual reality device having a housing containing a lens and a display operable to display an image to an eye of the user; and a long-pass filter arranged between the lens and the eye for examining the eye's ability to see the image, the long-pass filter having a first transmission region that transmits a visible light and a near-infrared light to the eye and a second transmission region that transmits the near-infrared light and blocks the visible light. In some aspects, the first transmission region includes a number of pinholes formed through the long-pass filter. In other aspects, the first transmission regions includes a number of etched regions on the long-pass filter. In still further aspects, the transmission of near-infrared light through the first transmission region and the second transmission region is substantially equal. In some aspects, the second transmission region surrounds the first transmission region. In further aspects, the long-pass filter is permanently or removably coupled to the virtual reality device. In some aspects, a dichroic filter is further contained within the housing. In other aspects, a camera is contained within the housing. The dichroic filter and the camera are arranged between the long-pass filter and the display.

In another aspect, an eye examination system is disclosed and includes a virtual reality device configured to be worn on a user's head, the virtual reality device having a housing containing a lens and a display operable to display an image to an eye of the user; a long-pass filter arranged between the lens and the eye for examining the eye's ability to see the image, the long-pass filter having a first transmission region that transmits a visible light and a near-infrared light to the eye and a second transmission region that transmits the near-infrared light and blocks the visible light; and one or more processors communicatively coupled to the virtual reality device, the one or more processors configured to receive a response regarding the eye's ability to see the image and determine a visual acuity of the eye. In some aspects, the processor determines a measurement of a sharpness of the image seen by the user's eye based on the response, and the measurement is used to determine the visual acuity of the eye. In other aspects, an eye tracking assembly having an emitter that emits the near-infrared light to the eye and a camera for tracking a movement of the eye based on a reflection of the near-infrared light, and wherein the tracked movement of the eye is used to select an operation of the virtual reality device. The system may further include a dichroic filter, and the dichroic filter and the eye tracking assembly are positioned between the long-pass filter and the display. In still further aspects, the first transmission region includes s a pinhole formed through the long-pass filter, or an etched region on the long-pass filter.

The second transmission region may entirely surround the first transmission region. The second transmission region blocks the visible light impinging on the filter from the display. The long-pass filter is permanently or removably coupled to the virtual reality device.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings, in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

FIG. 4 is a top plan view of an exemplary filter of FIG. 3.

FIG. 5 is a block diagram of an example system for measuring visual acuity using a VR headset including a filter.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

The terminology used herein is for the purpose of describing particular aspects only and is not intended to be limiting of the disclosure. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Figure 1:
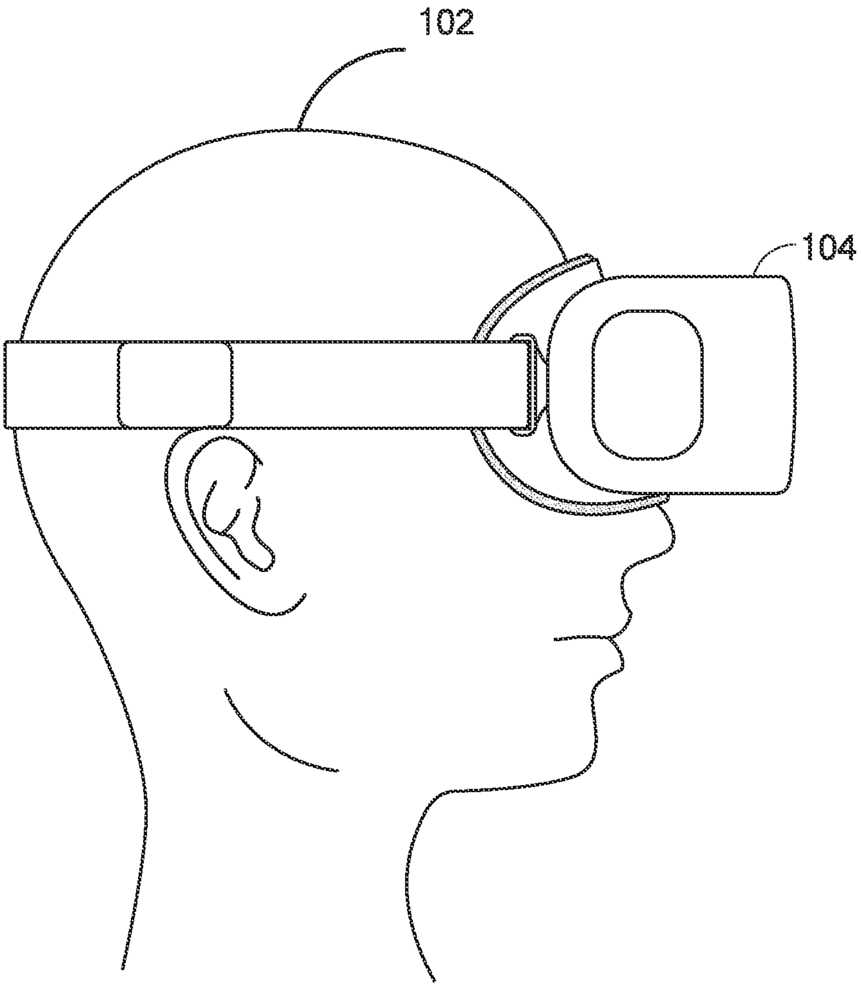
FIG. 1 depicts a user wearing a VR headset.

FIG. 1 depicts an eye examination system including a user (wearer) 102 wearing a virtual reality, VR, headset 104 which as modified below can be used to perform various ophthalmic examinations on the eyes of the wearer, including visual acuity testing for 20/20 vision or better. The modifications enable the use of a relatively low-cost solution in the form of an otherwise consumer grade VR headset.

Figure 2:
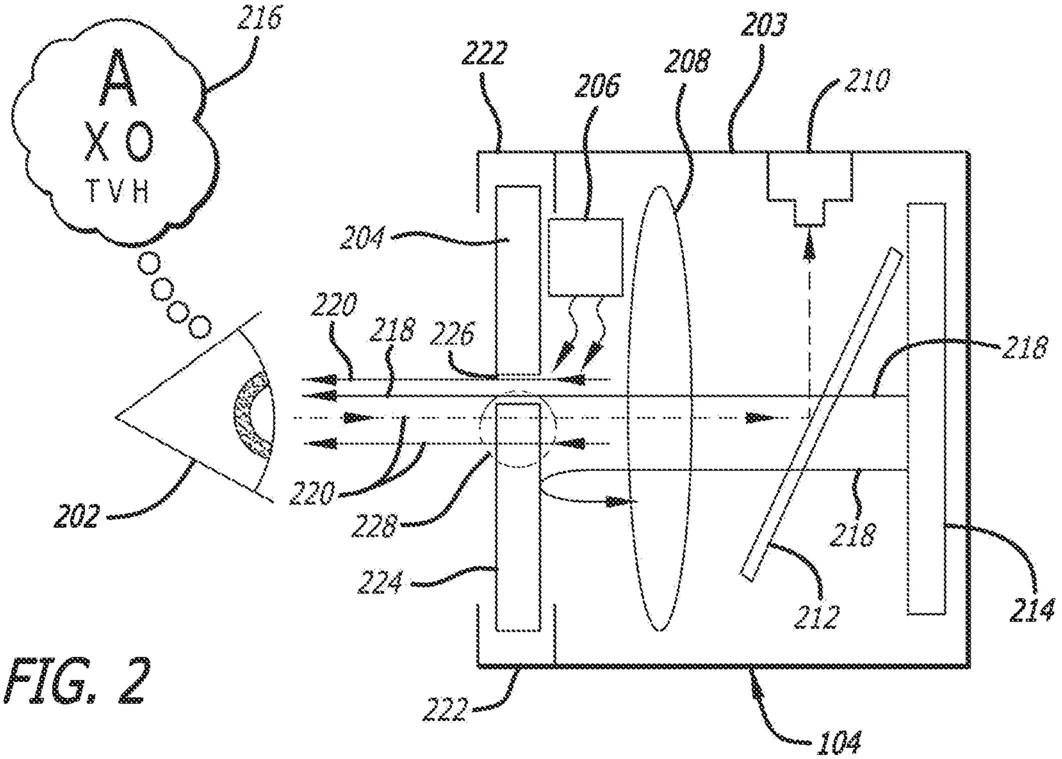
FIG. 2 is a cross-sectional side schematic view of an example system for measuring visual acuity using a VR headset including a filter.

FIG. 2 is a cross-sectional side schematic view of an example system for measuring visual acuity using a VR headset including a pinhole filter. From this view, it can be seen that when the VR headset 104 is positioned on the user's head (as shown in FIG. 1), the user's eye 202 is aligned with the various optical components of the VR headset 104 for performing an eye examination (e.g., a visual acuity test). Representatively, the VR headset 104 may include a housing 203 that contains, or is otherwise coupled to, the various optical components. In some aspects, the various optical components may include, among others, a filter 204, an illumination source 206, a VR lens 208, a dichroic filter 212, a camera 210 and a display 214. The display 214 may operate like a traditional VR display to display an image that is viewed by the eye 202 of the user. To conduct the eye examination, the display may display an image 216 such as an object, a symbol, a letter, or the like that the user can read or can otherwise be used to determine or measure a visual acuity of the eye 202. The VR lens 208 is further contained in the housing and operates to correct the angles of the light rays from the display 214 and direct them to the eye 202. In this aspect, the eye 202 perceives the image 216 on display 214 as much farther away than it actually is. For example, during the pinhole eye test, the image being viewed by the user should be from 14 to 20 feet away. Thus, VR lens 208 is configured to make the image 216 (e.g., object, symbol, letter, etc.) displayed on display 214 appear 14 to 20 feet away from the eye 202.

Dichroic filter 212 may be positioned between display 214 and VR lens 208. Dichroic filter 212 is angled relative to a path taken by visible light 218 that is emitted from display 214 and that passes through dichroic filter 212, before impinging on the eye 202. Dichroic filter 212 may also be angled so that it can reflect the near-infrared light 220 that is emitted toward eye 202 by illumination source 206 and has been reflected from the eye 202, towards the eye tracker camera 210.

Representatively, illumination source 206 may emit a near-infrared light 220 that reflects off of eye 202. For example, source 206 may be a light emitting diode that produces near-infrared (NIR) light, which illuminates eye 202 as shown. This NIR light is reflected off eye 202 and then travels through lens 208, followed by being reflected off a dichroic filter 212 and may form an NIR image for pick up by the eye tracker camera 210.

The eye tracker camera 210 may be an imaging device whose image data can then be processed by eye tracking software (that may be executed by a processor in the VR headset) to measure movement of the wearer's eye and track the direction of their gaze in real-time. For example, with the addition of electronics referred to here as eye movement interpretation logic that processes the image data produced by the eye tracker camera, the system enables hands-free feedback from the wearer of the headset during visual acuity testing.

Referring now in more detail to filter 204, filter 204 may be positioned between lens 208 and eye 202. Filter 204 is preferably positioned as close to eye 202 as possible. Representatively, in one aspect, filter 204 may be inserted within a receiving portion 222 of a portion of VR headset housing 104 closest to eye 202. In some aspects, filter 204 may be removably positioned within receiving portion 222 such that it may be removed and reinserted as desired by the wearer. In other aspects, filter 204 may be permanently or fixedly positioned, mounted or otherwise attached to receiving portion 222 such that it may not be removed by the wearer. In some aspects, filter 204 could be manually inserted/removed using a tab that pulls filter 204 away from lens 208 and then the user could push it back. In some aspects, this could also be automated so that filter 204 is electromechanically removed and inserted via a software command. Filter 204 may be an optical filter. For example, filter 204 may be a long-pass filter that includes a glass disk or substrate that transmit long wavelengths of light while blocking shorter wavelengths. Representatively, filter 204 includes glass disk or substrate 224. At least one or more pinholes 226 may be formed through glass disk or substrate 224. Both visible light 218 and near-infrared light 220 may pass through the pinholes 226 to eye 202. In this aspect, pinholes 226 may be considered as forming first transmission regions. The regions of substrate surrounding pinholes (e.g., glass regions) may also transmit near-infrared light 220 but will block visible light 218. For example, the glass regions surrounding pinholes 226 may be made of a colored glass or contain a coating that blocks or otherwise does not allow for the transmission of visible light. In this aspect, these regions may be considered as forming second transmission regions 228 that transmit near-infrared light 220 only. Second transmission region 228 may be considered to entirely surround the first transmission region formed by pinholes 226. In this aspect, the entire filter 204 (e.g., both regions 226 and 228) transmits some amount or frequency of light (e.g., near-infrared light 220) and there is no portion of filter 204 that blocks all light frequencies or is opaque.

Figure 3:
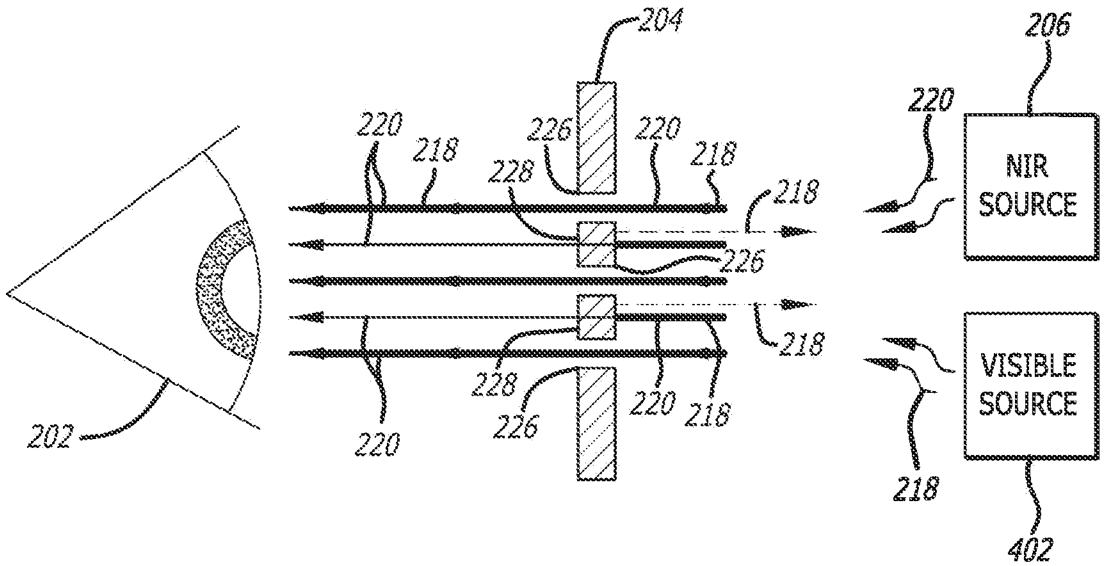
FIG. 3 is a cross-sectional side schematic view of an example system for measuring visual acuity using a VR headset including a filter.

Representatively, as illustrated in FIG. 3, filter 204 may include a number of pinholes 226 that are aligned with the eye 202. Pinholes 226 are dimensioned to allow for the transmission of both visible light 218 from a visible light source 402 (e.g., display 214) and near-infrared light 220 from a near-infrared light source 206, through filter 204 to the eye 202. The regions 228 surrounding the pinholes 226, on the other hand, block the transmission of visible light 218 and allow for the transmission of only near-infrared light 220 to eye 202 as shown. In this aspect, the pinhole test can be performed while still allowing the near-infrared light needed for eye tracking to be transmitted to eye 202. For example, the user may see a letter/number and then be asked to select which letter/number was shown by gazing at it via multiple choice selection, and eye tracking may be used to track the gaze.

FIG. 4 illustrates a top plan view of one representative configuration of filter 204. From this view, it can be seen that filter 204 may include a substantially circular or disk-shaped substrate or body portion 224. The body portion 224 may be made of a glass material or a coated material that blocks visible light while transmitting near-infrared light as previously discussed. An array of transmission regions or pinholes 226 may be formed through body or substrate portion 224. For example, pinholes 226 may be small circular holes that are cut through body or substrate portion 224. In this aspect, both near-infrared light and visible light can pass through pinholes 226 to eye 202. In other aspects, it is contemplated that instead of cutting holes entirely through body or substrate portion 224, the surface of body or substrate portion 224 may be etched to form pinhole like regions that due to the etching allow for the transmission of both visible and near-infrared light. In the case of etched pinhole like regions, the near-infrared transmission between all regions of the filter (e.g., regions formed by pinholes 226 and regions formed by body portion 224) may be approximately equal. In either case, the array of pinholes or pinhole like regions may be formed in any pattern or array suitable for transmitting the desired amount of light to the eye. In addition, the size or dimension of the pinhole or pinhole like regions may be any size or dimension suitable for conducting a visual acuity test such as the pinhole test as previously discussed.

Referring now to FIG. 5, FIG. 5 illustrates a block diagram of an example system for measuring visual acuity using a VR headset. Representatively, to perform the eye examination (e.g., visual acuity testing), system 500 may include headset 104 positioned on the user's head as previously discussed. Headset 104 may be communicatively coupled to a remote computer or other electronic device 502 allowing for control of the functions of headset 104 and for performing the eye examination. Representatively, remote device 502 may be equipped with a transmitter/receiver 504 for communicating (e.g., wireless internet communication) with headset 104. Device 502 may further include a processor 506 connected to a memory 508 that stores a software application for conducting refractive eye examinations. Using the software application, the medical professional may send an image 216 in the form of an eye chart, which is stored in database 510, to the software application so that the image 216 is displayed on the display of headset 104 for the user to see. The user may then indicate their ability to read the eye chart with their eyes (e.g., using the eye tracker camera to detect the eye movement). For example, the user may communicate their ability to read the eye chart to the headset software and then at the end of the test, the headset software would generate a report for the ECP. In other aspects, it is contemplated that the user could verbally indicate to the ECP (e.g., by a microphone) their ability to read the eye chart. The medical professional can communicate further instructions to the user via speakers (not shown) on headset 104 if applicable. If the image 216 seen by the user is blurry, the medical professional can choose another eye chart with a virtual correction imbedded in it. Different versions of the eye chart may be displayed to the patient until the displayed image is clear to the patient. The database 510 can store unlimited versions of the eye charts to compensate for any type of visual acuity related condition. Each eye chart corresponds to a distinct degree of correction when viewed by the wearer in headset 104. The eye charts in the form of images 216 can be displayed such that they are visible by both eyes, or only on a portion of the display visible by one eye, for testing of a single eye. The eye charts are created with the assumption that they will be viewed through the headset 104 at a defined distance from the eye, which may then be used to determine the visual acuity of the eye.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. For example, it should be understood that while a system having an eye tracker for automated wearer feedback is disclosed, the VR headset can also perform visual acuity testing but with manual or audible wearer feedback and the eye tracker camera is omitted. The description is thus to be regarded as illustrative instead of limiting.

What is claimed is:

1. An eye examination system comprising:

a headset configured to be positioned against a user's head, the headset having a housing containing a lens and a display operable to display an image to an eye of the user; and a long-pass filter arranged between the lens and the eye for examining the eye's ability to see the image, the long-pass filter having a first transmission region that transmits a visible light and a near-infrared light to the eye and a second transmission region that transmits the near-infrared light and blocks the visible light, wherein the first transmission region comprises a number of pinholes formed through the long-pass filter, and wherein the second transmission region is formed by a substrate portion of the long-pass filter that surrounds the first transmission region.

2. The system of claim 1 wherein the first transmission regions comprises a number of etched regions on the long-pass filter.

3. The system of claim 2 wherein the transmission of near-infrared light through the first transmission region and the second transmission region is equal.

4. The system of claim 1 wherein the long-pass filter is permanently coupled to the headset.

5. The system of claim 1 wherein the long-pass filter is removably coupled to the headset.

6. The system of claim 1 further comprising a dichroic filter contained within the housing and adapted to reflect the near-infrared light and transmit the image.

7. The system of claim 6 further comprising a camera contained within the housing, wherein the dichroic filter is adapted to reflect the near-infrared light towards the camera.

8. The system of claim 7 wherein the dichroic filter is positioned between the long-pass filter and the display and orientated to direct the near-infrared light towards the camera and pass the image from the display out through the lens and the long-pass filter.

9. An eye examination system comprising:

a headset configured to be positioned against a user's head, the headset having a housing containing a lens and a display operable to display an image to an eye of the user;

a long-pass filter arranged between the lens and the eye for examining the eye's ability to see the image, the long-pass filter having a first transmission region that transmits a visible light and a near-infrared light to the eye and a second transmission region that transmits the near-infrared light and blocks the visible light, wherein the first transmission region comprises a number of pinholes formed through the long-pass filter, and wherein the second transmission region is formed by a substrate portion of the long-pass filter that surrounds the first transmission region; and one or more processors communicatively coupled to the headset and to memory storing instructions that, when executed, configure the one or more processors to receive a response regarding the eye's ability to see the image and determine a visual acuity of the eye.

10. The system of claim 9 wherein the instructions further configure the one or more processors to determine a measurement of a sharpness of the image seen by the user's eye based on the response, and the measurement is used to determine the visual acuity of the eye.

11. The system of claim 9 further comprising an eye tracking assembly having an emitter that emits the near-infrared light to the eye and a camera for tracking a movement of the eye based on a reflection of the near-infrared light, and wherein the tracked movement of the eye is used to select an operation of the headset.

12. The system of claim 11 further comprising a dichroic filter, and wherein the dichroic filter and the eye tracking assembly are positioned between the long-pass filter and the display.

13. The system of claim 9 wherein the first transmission regions comprises an etched region on the long-pass filter.

14. The system of claim 9 wherein the second transmission region blocks the visible light impinging on the filter from the display.

15. The system of claim 9 wherein the long-pass filter is permanently coupled to the headset.

16. The system of claim 9 wherein the long-pass filter is removably coupled to the headset.

17. The eye examination system of claim 1, further comprising:

one or more processors communicatively coupled to the headset; and memory coupled to the one or more processors, the memory storing instructions that, when executed by the one or more processors, cause the eye examination system to perform operations including:

receiving a response regarding the eye's ability to see the image; and determining a visual acuity of the eye.

18. The eye examination system of claim 1, wherein the second transmission region is not opaque to the near-infrared light.

* * * * *